United States Patent [19]

Ausikaitis et al.

[11] 4,373,935
[45] Feb. 15, 1983

[54] ADSORPTION SEPARATION CYCLE

[75] Inventors: Joseph P. Ausikaitis, White Plains; Desh R. Garg, Hopewell Junction, both of N.Y.

[73] Assignee: Union Carbide Corporation, Danbury, Conn.

[21] Appl. No.: 259,377

[22] Filed: May 1, 1981

[51] Int. Cl.³ .............................................. B01D 53/04
[52] U.S. Cl. ............................................ 55/33; 55/75; 203/19; 203/41; 210/689; 568/917
[58] Field of Search ......................... 55/33, 35, 62, 75; 202/42; 203/18, 19, 41; 210/689; 568/916, 917

[56] References Cited

U.S. PATENT DOCUMENTS

| | | | |
|---|---|---|---|
| 1,985,204 | 12/1934 | Derr et al. | 203/41 X |
| 1,985,205 | 12/1934 | Derr | 55/35 |
| 2,137,605 | 11/1938 | Derr | 55/33 |
| 2,944,627 | 7/1960 | Skarstrom | 55/75 X |
| 3,122,486 | 2/1964 | Skarstrom | 202/42 |
| 3,132,079 | 5/1964 | Epperly et al. | 203/41 |
| 3,728,844 | 4/1973 | Snyder et al. | 55/62 X |
| 3,839,847 | 10/1974 | Banikiotes et al. | 55/62 X |
| 4,233,038 | 11/1980 | Tao | 55/33 |
| 4,273,621 | 6/1981 | Fornoff | 55/33 X |

*Primary Examiner*—Robert H. Spitzer
*Attorney, Agent, or Firm*—Richard G. Miller

[57] ABSTRACT

An efficient fixed-bed vapor-phase adsorption cycle for bulk separations wherein the heat front generated by the exothermic heat of adsorption is maintained in the bed either in or behind the mass transfer zone, and is subsequently used in the desorption/regeneration step. The cycle is especially useful in drying mixtures of water and compounds which form azeotropes with water as well as the azeotropes themselves, such as 190-proof ethanol.

11 Claims, 4 Drawing Figures

ADSORPTION SEPARATION CYCLE

The present process relates in general to the bulk separation of mixtures by selective adsorption of at least one principal constituent thereof using crystalline zeolitic molecular sieve adsorbents. More particularly the process concerns the vapor phase drying of water-organic azeotropes such as water-ethanol mixtures by size-selective adsorption of the water constituent on an appropriate molecular sieve zeolite using a fixed-bed adsorption system and an adsorption-desorption cycle which utilizes the water heat of adsorption of the adsorption stage in the desorption stage.

In general, drying of fluids, either gases or liquids, by the selective adsorption of the water is economically feasible only when the concentration of water in the fluid is small, i.e. present at a level of a few parts per million up to about 2.5 weight percent. When larger concentrations of water must be removed from a normally vapor-phase mixture, then gas-liquid absorption or refrigeration is ordinarily resorted to. When such relatively large concentrations of water are to be removed from normally liquid mixtures, distillation procedures are most commonly used. This is not because selective adsorption is incapable of producing a sufficiently water-free product, but rather is due to the fact that the adsorbent's capacity for water is finite and only a fraction of the mass of the adsorbent. It is necessary, therefore, in order to avoid the use of unduly large quantities of adsorbent, to use a smaller and reasonable mass of adsorbent and to periodically and frequently regenerate it by desorption of at least some of its water loading in order to suitably treat more of the water-containing feedstock. The greater the water concentration of the feedstock, of course, the more frequent the need for regeneration of a given mass of adsorbent. Moreover, to provide for a more or less continuous output of dried product, multiple adsorbent beds must be used, so that when the adsorbent capacity of one bed is exhausted, a fresh bed is placed on stream and the exhausted bed regenerated.

The major energy requirements for such an adsorption process is the regeneration step, where a regeneration fluid must be heated to provide the energy for the endothermic desorption of water, the energy required to raise the adsorbent temperature, the energy required to heat the carrier fluid in the voids, and the energy required to heat up the portion of the vessel in contact with the adsorbent. Because regenerations must be carried out more frequently for high water concentrations, the inefficiencies of energy consumption of an adsorptive process are thus more pronounced compared to alternative processes. These constraints generally limit the applicability of adsorptive drying process to small concentrations of water or to unique applications where alternatives are not feasible for other reasons.

One such application in which the alternative process lack clear superiority to adsorptive bulk drying, is azeotrope liquid drying. In treating these mixtures, extractive or vacuum distillation techniques, which are far more complex and energy-intensive than simple distillation, are required. Nevertheless such alternative processes are still generally preferred over liquid-phase adsorption drying for several reasons; especially when a continuous process operation is required, as usually is the case. More particularly, where ordinary economic considerations limit the quantities of adsorbent and the number of adsorbent beds which can be employed, continuous adsorption processes of necessity operate using relatively short adsorption and regeneration cycle times. Product recovery thus becomes critical because one bed void-space volume of feedstock must be removed from each bed during each regeneration stage. Since a liquid has a high molar density, it is extremely difficult to move about in the adsorption system within the short cycle times imposed.

Although most of the difficulties inherent in liquid-phase bulk drying adsorption processes can be avoided by operating the cycle in the vapor phase, the high water concentration of the feedstock leads to another phenomenon which has heretofore been considered so adverse to the stability and predictability of adsorption separation processes that it has been avoided at all costs by those skilled in the art.

The phenomenon is commonly referred to as "cross-over," and concerns the relative positions in an adsorbent bed of a mass transfer front and a heat front. In the adsorptive drying of a fluid stream as in the present invention, the heat front is created by the heat of adsorption of water. For zeolite adsorbents, about 1,800 BTU's are liberated for every pound of water adsorbed. The heat is generated in the water mass-transfer front which is the interfacial region in an adsorption column between water-saturated adsorbent and activated (or partially activated) adsorbent. For small water concentrations ($\leq 2.5$ wt.-%), the heat generated in the front is carried out and ahead of the front by the carrier fluid which is moving at a much higher velocity than the water adsorption front in the bed. This may cause the product fluid to be slightly warmer than the feed fluid but does not affect the adsorption dynamics within the mass transfer front. For high water concentrations (2.5 to 50 wt.-%), heat generated can remain within the mass transfer front or is deposited behind the mass transfer front. In such cases the rate at which heat is generated by the adsorption exotherm is greater than the rate that it is carried out of the mass transfer front by the carrier fluid, i.e. the mass transfer front "crosses over" the heat front. Thereafter, adsorption is being carried out at a higher temperature than the feed temperature and reduces the efficiency of the adsorbent for water removal by both lowering the effective water equilibrium capacity and elongating the mass-transfer front, which can cause early breakthrough of water into the product. For these cases the mass transfer front is unstable and its behavior is highly unpredicatable for design purposes.

The simple equation set form below is useful in determining the approximate location of the heat front relative to the location of the mass transfer front in an adsorption bed:

$$R = \frac{(Xi - Xo)}{(Yi - Yo)} \times \frac{Cp(g)}{Cp(s)}$$

wherein R is the "cross-over ratio;" Xi is the adsorbent loading in equilibrium with the feed concentration of adsorbate behind the mass transfer front in terms of lbs. adsorbate per lbs. adsorbent; Xo is the adsorbent residual loading ahead of the mass transfer front which is the result of a previous regeneration step in terms of lbs. adsorbent per lb. adsorbate; Yi is the inlet (feed) adsorbate concentration in terms of lbs. adsorbate per lb. of carrier fluid; Yo is the adsorbate concentration of the bed effluent in equilibrium with Xo in terms of lbs. adsorbate per lb. carrier fluid; Cp(g) is the heat capacity of the carrier fluid in terms of BTU's per lb. of fluid per degree Fahrenheit; and $Cp_{(s)}$ is the heat capacity of the adsorbent bed solids in terms of BTU's per lb. of solids per degree Fahrenheit.

Thus for a zeolite adsorbent system, for values of "R" greater than 5, the heat front is far ahead of the mass transfer front, and heat will normally leave the adsorbent bed before the leading edge of the mass transfer front leaves the bed. For values of "R" of from about 1 to 5, the heat front is located within the mass transfer front between the leading edge and the stoichiometric point of the first mass transfer front created in the bed, and for values of 0.5 to 1, the heat front is located behind the stoichiometric point of the first mass transfer front. The initial (starting) bed temperature and the total pressure of the system also have a slight affect upon the crossover ratio "R."

Operating an adsorption process for which "R" = <5 results in a reduction of dynamic adsorption capacity compared with the capacity predicted from isothermal data. Thus the heat generated both lengthens the mass transfer front and lowers the equilibrium capacity because of higher local operating temperature. The heat generated can be distributed throughout the adsorbent bed as a broad pulse or a narrow spike. The maximum temperature experienced is a function of "R," the adsorption dynamics and the initial adsorbent conditions. This temperature must be kept below some maximum level because of the potential destruction of the adsorbent or chemical reaction of the fluid at these extreme temperatures.

Surprisingly, it has now been discovered that despite the adverse consequences of the "crossover" mode of operation, the bulk separation of water from admixture with organic compounds can be commercially feasible using a process involving selective adsorption of the water constituent on zeolitic molecular sieves. To accomplish this result, the present process overbalances the inefficiency of the unavoidable non-isothermal adsorption step by utilizing the heat energy generated to create a more efficient thermal regeneration step, with the net result being an efficient overall process cycle.

Accordingly, the process of the present invention comprises:

(a) passing in the vapor phase a feedstock comprising at least 2.5 weight percent water in admixture with at least one organic molecular species into a fixed adsorption bed at a temperature and pressure which prevents the capillary condensation of said organic molecular species, said fixed adsorption bed containing an adsorbent mass consisting essentially of a crystalline zeolitic molecular sieve adsorbent, small enough to substantially exclude the said organic molecular species, moving the water adsorption mass transfer front and the coinciding or trailing heat front created in said fixed bed along said bed toward the effluent end thereof to a predetermined point short of breakthrough of either of said front, at least that portion of said molecular sieve adsorbent contacted by said water mass transfer front containing adsorbed thereon, prior to and at the time of contact of said front, at least about 2, and preferably at least about 5, weight percent water, said molecular sieve adsorbent having a capacity for the adsorption of water under the imposed operating conditions greater than the water loading thereon at the time of contact by the water mass-transfer front;

(b) from the effluent end of said bed, recovering a product stream containing a lower concentration of water than the feedstock;

(c) terminating the flow of feedstock into said bed prior to breakthrough of either of the heat front and the water mass transfer front, and prior to substantial loss of the heat energy from the bed, commencing the countercurrent passage through said bed of an essentially non-sorbable purge gas at a temperature within about 25° F. of the temperature of, and substantially at the same pressure as, the feedstock entering the bed during adsorption step (a), said temperature and pressure being sufficient to prevent capillary condensation of the said organic molecular species of said feedstock, whereby said heat front is moved back through said bed and utilized in desorbing water from the adsorbent mass;

(d) continuing the countercurrent purging of said bed until the water loading on said adsorbate is essentially the same as at the beginning of adsorption step (a); and (e) repeating adsorption step (a).

The adsorption dynamics of a typical adsorption step of this process are illustrated in the graphic formulae which appear as FIGS. 1 through 3 of the drawings.

Figure 1:
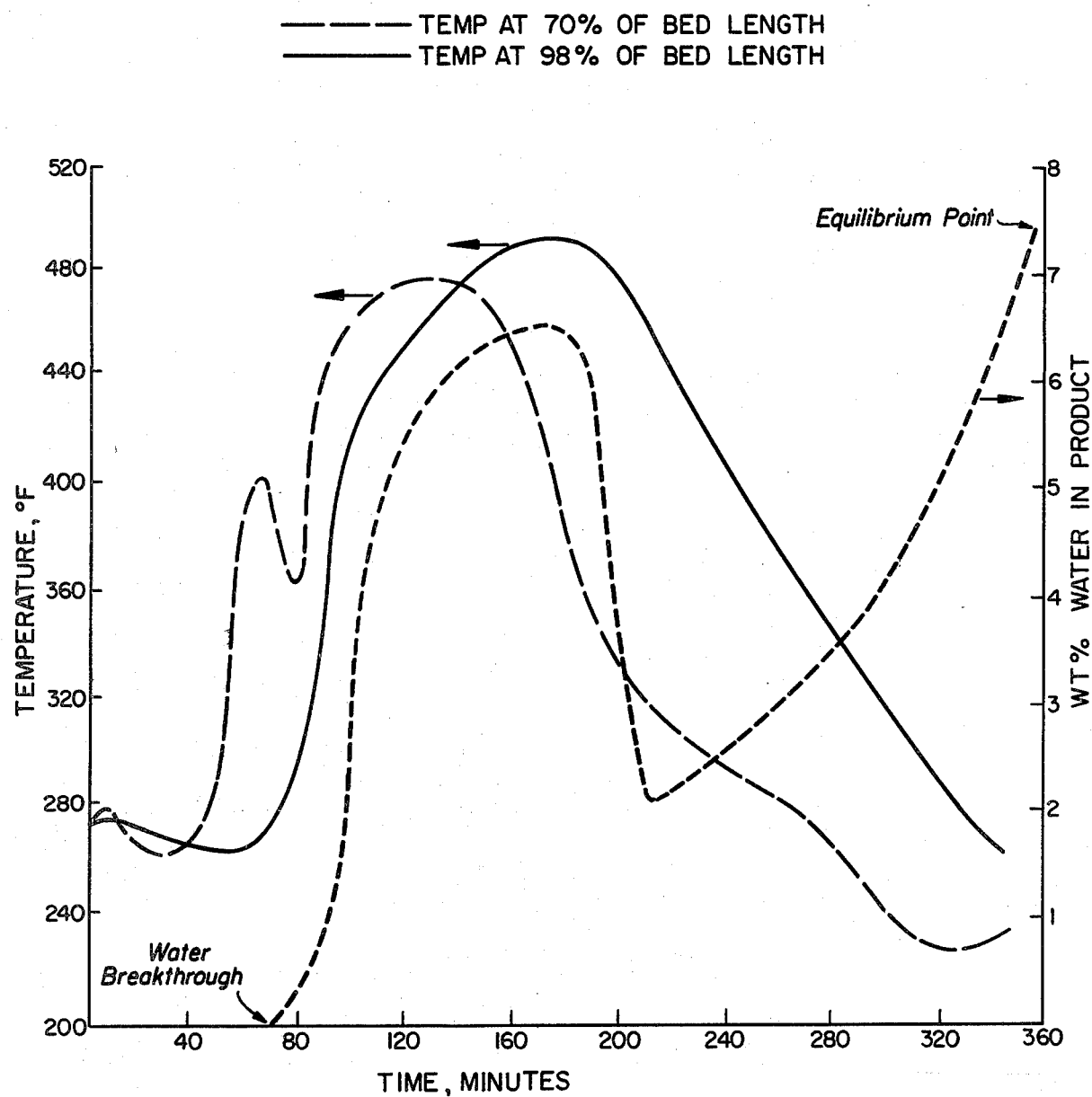
FIG. 1 is a plot of the variations with increasing time of the water content of the effluent from an adsorption bed used to dry 190 proof ethanol. The temperature profile with increasing time of two positions along the length of the adsorbent bed is also shown.

With respect to FIG. 1, the adsorption bed contains as the sole adsorbent a potassium-exchanged form of zeolite A which has pore diameters of approximately 3 Angstroms. This adsorbent, which was pre-loaded with 5 wt.-% water, adsorbs water but excludes the ethanol from the 190 proof ethanol feedstock which was fed to the bed at a temperature of 250° F. and under a pressure of 20 psia. Water concentrations in the bed effluent in excess of the equilibrium concentration under the conditions imposed, i.e. water breakthrough, appeared after about 70 minutes. This indicates that a first adsorption front has been established and has traversed the length of the bed. With continuation of the adsorption step the water concentration in the effluent increases very rapidly to a first maximum value of about 6.4 weight percent after about 180 minutes and then decreases even more rapidly to a minimum of about 2 weight percent, whereupon the water content of the bed effluent again reverses direction and continues to increase up to the maximum attainable concentration, i.e. the equilibrium point of about 7.5 weight-percent. This behavior clearly shows that a two-zone unstable mass-transfer of water occurred during the adsorption step which is attributable to the crossover of the heat front and the first water mass transfer zone. This phenomenon is further established by the plots of the temperature profiles at points 70 percent and 98 percent, respectively, along the bed length toward the effluent end. A small and insignificant heat pulse is immediately created and very quickly passes through and out of the bed. The principal heat front, however, remains behind the water mass-transfer front, and at a point 70% along the bed, the maximum temperature of about 470° F. is not reached until shortly before the stoichiometric point of the first water mass transfer zone leaves the bed. After about 165 minutes of the adsorption step the maximum concentration of water in the effluent and the maximum temperature at a point 98% along the bed length are reached, clearly showing the coincident or slightly trailing behavior of the heat front relative to the first mass transfer zone.

Figure 2:
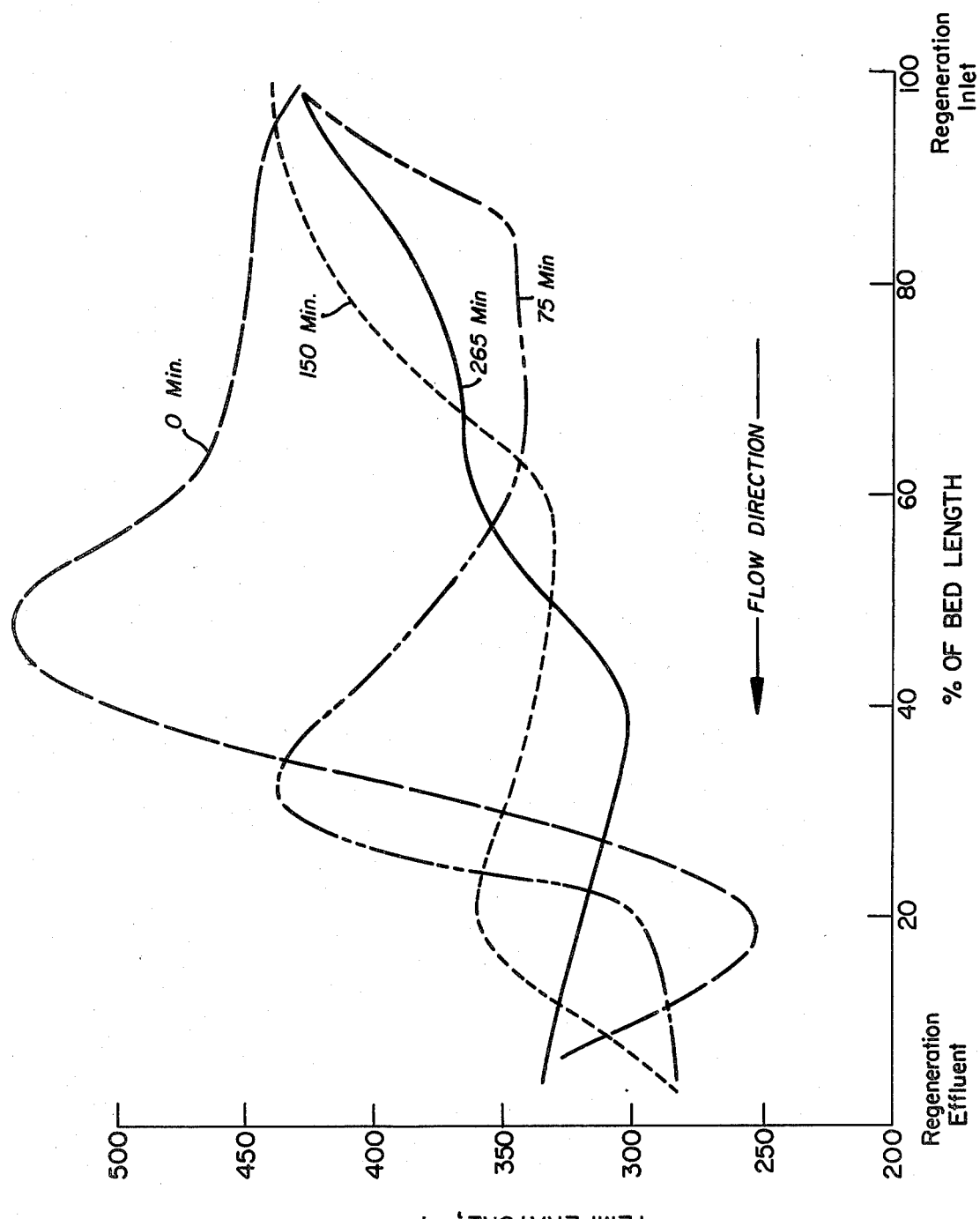
FIG. 2 is a plot of the temperature profile of the bed of FIG. 1 when regenerated countercurrently and immediately after the 360-minute adsorption step with a heated purge gas.

If after the initial breakthrough of water from the bed in FIG. 1 i.e. at about 70 minutes after the start of the adsorption step, regeneration with a non-adsorbable purge gas at 450° F. is commenced immediately and in a countercurrent direction, the regeneration profiles are those shown in the plot of FIG. 2. The peak internal bed temperature moves backward through the bed and decreases to the original bed temperature due to the utilization of this heat energy to desorb the adsorbed water. If, however, a substantial amount of the thermal energy of the bed is allowed to escape to the surroundings after an adsorption step of FIG. 1, then the temperature profile are those shown in FIG. 3.

Figure 3:
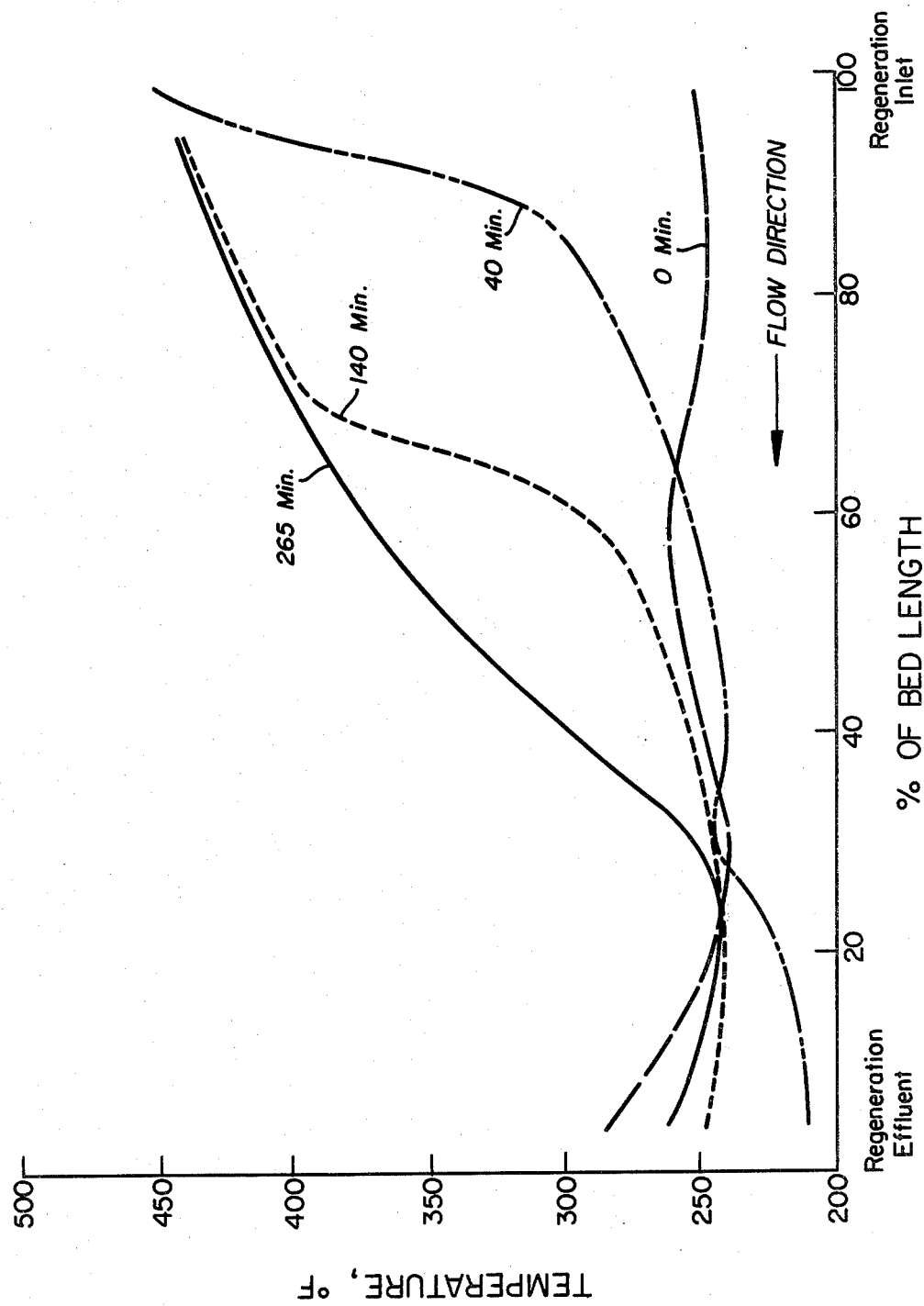
FIG. 3 is a plot of the temperature profile of the bed of FIG. 1 when regenerated as in FIG. 3, except that the temperature peaks have been dissipated to the external surroundings of the bed.

If in both cases shown in FIGS. 2 and 3, the same volume of purge gas at 450° F. is supplied to each bed, the benefits of using the adsorptive heat rise to augment regeneration is clearly demonstrated by a comparison of the effective capacity of the adsorbent bed in each case for the subsequent adsorption step. These results are given below along with the experimental conditions:

| REGENERATION: | |
|---|---|
| Regeneration Flow Rate | 400 SCFH of $N_2$ saturated with $H_2O$ at 95° F. |
| Regeneration Inlet Temperature | 450° F. |
| Regeneration Pressure | 20 PSIA |
| Regeneration Time | 270 minutes |
| ADSORPTION: | |
| Adsorbent Bed Weight | 38.2 pounds |
| Column Diameter | 3 inches |
| Feed Flow Rate of Azeotrope | 200 cc/min |
| Water Concentration of Azeotrope | 7.58 wt. % |
| Feed Temperature | 250° F. |
| Feed Pressure | 20 PSIA |
| WATER BREAKTHROUGH TIME: | |
| With Adsorptive Heat Rise Benefit | 60 minutes |
| Without Adsorptive Heat Rise Benefit | 35 minutes |

As used herein the terms mass transfer front, heat front and breakthrough are all intended to have the meaning conventional in the adsorption-separation art. The mass transfer front is the fluid concentration or adsorbent loading profile of the adsorbable component over the mass transfer zone. The adsorbate loading through the transfer zone is a linear function of the fluid phase concentration of the adsorbable component. Similarly the heat front is the maximum temperature profile of the adsorbent generated by the heat of adsorption of the adsorbable component—in the present case, water. Breakthrough is said to occur when the leading edge of the mass transfer front or the heat front reaches the effluent end of the bed. Breakthrough is, however, arbitrarily defined, and can be taken as either the minimum detectable concentration or temperature increase in the effluent product or as the maximum allowable increase in these parameters. In the present process, the latter criterion is applied.

The particular species of crystalline zeolitic molecular sieve employed is not a narrowly critical factor. In all event, however, it should be capable of adsorbing more than 2, preferably more than 5, weight percent water under the process conditions of temperature and pressure, and to substantially exclude from adsorption essentially all of the other constituents of the feedstock under those conditions. As will be readily understood by those skilled in the art, the significant adsorption of such materails other than water can be disruptive of the process by, for example, the creation of secondary mass transfer and heat fronts or by partially decomposing on the zeolite and diminishing its adsorptive capacity through coke formation. Thus a zeolite having an effective pore diameter of about 3 Angstroms, such as the potassium cation form of the type A zeolite, is suitable for all feedstocks with the present process, but where the organic constituent is a relatively large molecule, such as benzene, any of the so-called small pore zeolites such as the various cationic forms of zeolite A, zeolite F, zeolite D, zeolite W, zeolite alpha, zeolite phi, mordenite, erionite, clinoptilolite and chabazite can be suitably employed. A comprehensive listing of both synthetic and naturally occurring zeolites is set forth in "Zeolite Molecular Sieves," by D. W. Breck, John Wiley & Sons, New York, NY (1974). A zeolite species of universal applicability in treating the feedstocks of the present process is the potassium-exchanged form of zeolite A in which the pores are about 3 Angstroms in diameter. The type A zeolite structure, moreover, has a very large capacity for the adsorption of water. For most feedstocks, including those in which the organic constituent is ethanol or a higher alcohol, small pore mordenite, particularly the mineral form, such as is commercially available under the Union Carbide Corporation designation AW-300, is also highly effective and is a preferred adsorbent.

The feedstocks suitably treated are any mixtures of water with one or more organic compounds which contain at least 2.5 weight percent water. Preferred feedstocks are those which cannot be dried by conventional distillation techniques, i.e., are either aqueous azeotropes or can form azeotropic mixtures by appropriate changes in the relative proportions of their constituents. Such mixtures include those wherein the organic constituent is ethanol, iso-propanol, sec-butanol, tert-butanol, allyl alcohol, benzene, toluene, diethyl ether, di-iso-propyl ether, ethylene chloride, n-propyl formate, ethyl acetate, methyl propionate, ethyl-iso-butyrate, n-propyl nitrate, methyl ethyl ketone, formic acid, and pyridine. Particularly preferred feedstocks are mixtures of one or more primary alcohols having from 2 to 5 carbon atoms inclusive with water in which the water content is from 2.5 to about 20 weight percent. Above about 20 weight percent water the adsorption-desorption cycle times become undesirably short and heat rise peaks in the bed are also higher than preferred. An especially preferred feedstock is an ethanol-water mixture containing from about 3.5 to volume-% (4.4 to 14.3 weight-%) water.

The temperature and pressure conditions for the adsorption step must be selected to maintain the feedstock in the vapor phase and prevent capillary condensation of the organic constituent in the bed. It is preferred that the feedstock temperature be within the range of about 200° F. to 450° F. and at an appropriate corresponding pressure within the range of about 1 atmosphere (absolute) up to about 100 psia. At higher pressures it is possible for the density of the feedstock to be sufficiently high to force the heat front ahead of the water mass-transfer front. During the countercurrent purge-desorption step the temperature of the non-sorbable purge gas entering the bed can be from about 200° to 475° F., and is preferably within 25° F. of the temperature of the feedstock stream during adsorption. The adsorption-desorption cycle is preferably isobaric or nearly isobaric, i.e. the desorption step is essentially thermal swing rather than the pressure swing type.

The purge gas utilized in the desorption/regeneration stages of the process can be any vapor phase compound which is not harmful to the zeolite adsorbent, does not appreciably react with the feedstock constituents under the imposed conditions and which is not appreciably adsorbed by the zeolite. The non-adsorbability of the purge gas can be due either to molecular size exclusion or to a weak adsorptive attraction between it and the zeolite. Thus purified product from a previous adsorption step can be used or, and preferably, a normally gaseous extraneous medium such as nitrogen, hydrogen, helium, carbon dioxide or methane.

In carrying out the purge-desorption steps it is important that the regenerated bed contains sufficient residual adsorbed water so that during the following adsorption step of the cycle that portion of the molecular sieve adsorbent contacted by the water mass transfer front which develops contains, prior to and at the time of contact, at least about 2, and preferably at least about 5 weight percent water. Accordingly, it is not essential that the entire bed have a level loading of water, and in fact as a practical matter it will not. Since the water loading on the egress end of the bed during adsorption determines the concentration of water in the product, it can be advantageous to carry out the countercurrent purge-desorption in such a manner as to minimize the water loading beyond the point along the bed length reached by the water mass transfer front, while assuring that the adsorbent actually passed over by that mass transfer front contains the requisite amount of water loading to prevent unduly high thermal peaks.

The process is illustrated by the following specific embodiment described with reference to FIG. 4 of the drawings.

EXAMPLE 1

Figure 4:
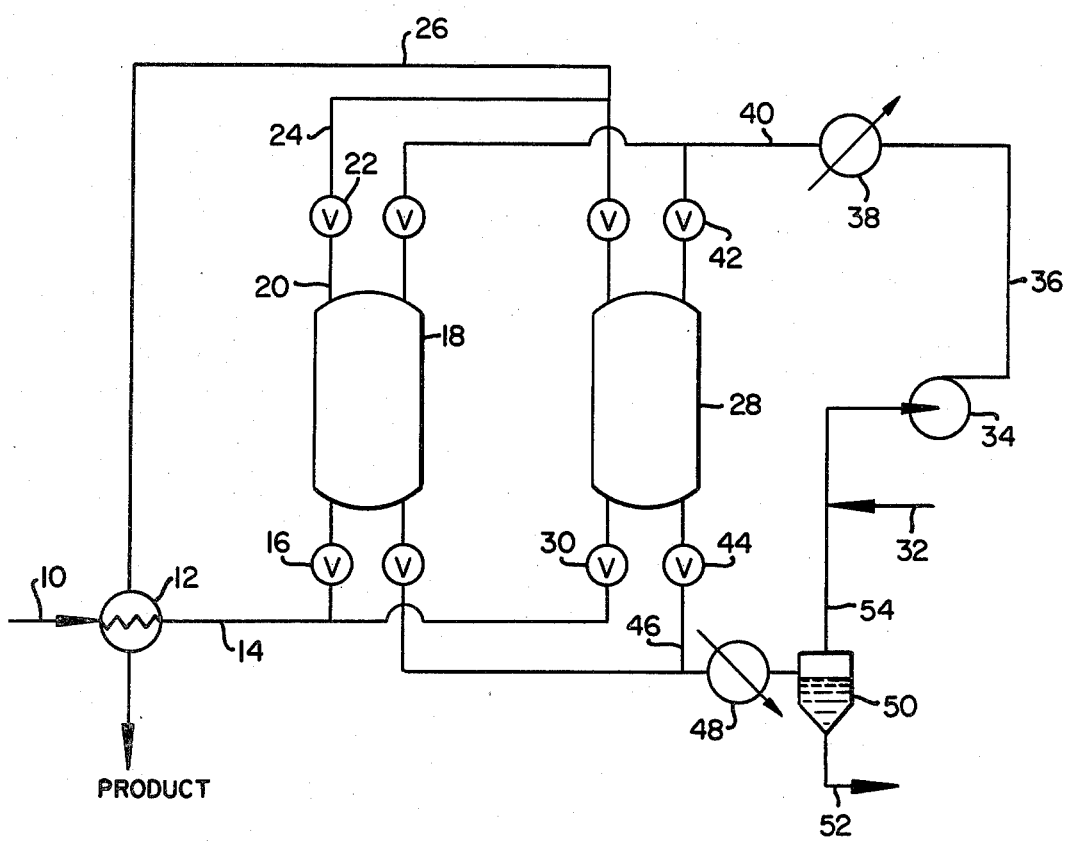
FIG. 4 is a flow diagram showing a process embodiment typical of the present invention.

With reference to the adsorption system shown in FIG. 4, the adsorption beds 18 and 28 are each packed with 1500 lbs. of ⅛" pellets of Type 3A zeolite, which, under the process conditions utilized herein, are capable of dehydrating 5 million gallons (4100 pounds/hour) of 190 proof ethanol feedstock to a 199 proof ethanol product. Feedstock 190 proof ethanol is fed into the system at the rate of 99.4 pound moles per hour through line 10 and heat exchanger 12 where the temperature is raised to 300° F., and thereafter through line 14, valve 16 and thence into bed 18. As a result of the most recent purge regeneration, the adsorbent in bed 18 contains a residual water loading of 11.5 weight percent. The pressure throughout the system is approximately 40 psia. In bed 18 the water of the feedstock is adsorbed forming a mass transfer front which moves upward therethrough. The water loading behind the mass transfer front is about 17 weight percent, and as a consequence a significant heat rise of approximately 100° F. occurs resulting in the formation of a heat front which slightly trails the water mass transfer front. The adsorption step in bed 18 is continued for about 15 minutes during which period product 199 proof ethanol is recovered as the bed effluent though line 20, valve 22, line 24 line 26 and heat exchanger 12. At the end of the 15-minute adsorption step, during which period neither the water mass transfer front nor the heat front have broken through the bed 18, the feedstock is diverted to bed 28 through line 14 and valve 30. Bed 18 is thereupon regenerated in the same manner as bed 28 was during the previous 15-minute period. At the beginning the regeneration step, bed 28 is in the same condition as bed 18 is at this point. The regeneration is accomplished using $CO_2$ as a purge gas introduced into the system through line 32. Line 32 also serves as the means to introduce make-up purge gas into the operating system as required. The purge gas is forced at a pressure of 40 psia by blower 34 through line 36, heater 38 where its temperature is raised to 300° F. line 40, valve 42 into bed 28 in a flow direction countercurrent to the direction of flow of the feedstock stream thereinto. The initial action of the $CO_2$ purge gas stream is to flush the void space of the bed and thereafter to partially desorb the zeolite adsorbent. Purge gas and desorbed water leave the bed 28 through valve 44, line 46 and are passed through cooler 48 wherein the temperature is lowered to 95° F. and water is condensed and collected in knock-out 50. Water is removed from the system through line 52 and the $CO_2$-water vapor mixture is recycled to blower 34 through line 54, reheated to 300° F. and again used to purge bed 28. The flow rate of $CO_2$ through the purge loop is 490 mols/hr. The purge regeneration stage is 15 minutes as in the case of the adsorption stage.

What is claimed is:
1. Adsorption separation process which comprises;
   (a) passing in the vapor phase a feedstock comprising at least 2.5 weight percent water in admixture with at least one organic molecular species into a fixed adsorption bed at a temperature and pressure which prevents the capillary condensation of said organic molecular species, said fixed adsorption bed containing an adsorbent mass consisting essentially of a crystalline zeolitic molecular sieve adsorbent, small enough to substantially exclude the said organic molecular species, moving the water adsorption mass transfer front and the coinciding or trailing heat front created in said fixed bed along said bed toward the effluent end thereof to a predetermined point short of breakthrough of either of said fronts, at least that portion of said molecular sieve adsorbent contacted by said water mass transfer front containing adsorbed thereon, prior to and at the time of contact of said front, at least about 2 weight percent water, said molecular sieve adsorbent having a capacity for the adsorption of water under the imposed operating conditions greater than the water loading thereon at the time of contact by the water mass-transfer front;
   (b) from the effluent end of said bed, recovering a product stream containing a lower concentration of water than the feedstock;
   (c) terminating the flow of feedstock into said bed prior to breakthrough of either of the heat front and the water mass transfer front, and prior to substantial loss of the heat energy from the bed, commencing the countercurrent passage through said bed of an essentially non-sorbable purge gas at a temperature within about 25° F. of the tempera- ture of, and substantially at the same pressure as, the feedstock entering the bed during adsorption step (a), said temperature and pressure being sufficient to prevent capillary condensation of the said organic molecular species of said feedstock, whereby said heat front is moved back through said bed and utilized in desorbing water from the adsorbent mass;

(d) continuing the countercurrent purging of said bed until the water loading on said adsorbate is essentially the same as at the beginning of adsorption step (a), and (e) repeating adsorption step (a).

2. Process according to claim 1 wherein the feedstock is a mixture of water and an organic molecular species which can form an azeotrope.

3. Process according to claim 2 wherein the organic molecular species is a member selected from the group consisting of ethanol and isopropanol.

4. Process according to claim 1 wherein the feedstock is an azeotrope.

5. Process according to claim 4 wherein the organic species is a member selected from the group consisting of ethanol and isopropanol.

6. Process according to claim 1 wherein the organic molecular species is a primary alcohol containing from 2 to 5 carbon atoms inclusive.

7. Process according to claim 6 wherein the temperature of the feedstock entering the adsorption bed is within the range of 200° F. to 450° F. and the pressure is within the range of about 1 to about 6.8 atmospheres.

8. Process according to claim 7 wherein the zeolitic molecular sieve adsorbent is a zeolite having the mordenite crystal structure.

9. Process according to claim 7 wherein the zeolitic molecular sieve adsorbent is a Type A zeolite having pore diameters of about 3 Angstroms.

10. Process according to claim 7 wherein at least that portion of the molecular sieve adsorbent in the adsorption bed which is contacted by the water mass transfer front during step (a) contains, prior to and at the time of contact of said front, at least 2 weight percent water.

11. Process according to claim 10 wherein the feedstock is a mixture consisting essentially of water and ethanol wherein the water content is from 5 to 12 volume percent of the overall mixture.

* * * * *